(12) United States Patent
Yu et al.

(10) Patent No.: US 6,544,249 B1
(45) Date of Patent: Apr. 8, 2003

(54) BIOLOGICAL MICROFISTULA TUBE AND IMPLANTATION METHOD AND APPARATUS

(75) Inventors: Dao-Yi Yu, Perth (AU); William Huxley Morgan, Perth (AU)

(73) Assignee: The Lions Eye Institute of Western Australia Incorporated, Nedlands (AU)

( * ) Notice: Subject to any disclaimer, the term of this patent is extended or adjusted under 35 U.S.C. 154(b) by 0 days.

(21) Appl. No.: 09/319,028

(22) PCT Filed: Nov. 28, 1997

(86) PCT No.: PCT/AU97/00811

§ 371 (c)(1), (2), (4) Date: Jul. 15, 1999

(87) PCT Pub. No.: WO98/23237

PCT Pub. Date: Jun. 4, 1998

(30) Foreign Application Priority Data

Nov. 29, 1996 (AU) .............................. PO 3944

(51) Int. Cl.⁷ .......................... A61M 31/00; A61M 5/00
(52) U.S. Cl. .......................... 604/521; 604/8; 623/1.41; 606/166
(58) Field of Search .................. 604/8, 93.01, 264, 604/265, 272, 521, 523, 540–541; 623/1.11, 1.41; 606/166, 108, 167

(56) References Cited

U.S. PATENT DOCUMENTS

| 3,788,327 A |   | 1/1974  | Donowitz et al. |
|-------------|---|---------|-----------------|
| 4,804,382 A | * | 2/1989  | Turina et al.   |
| 4,820,626 A | * | 4/1989  | Williams et al. |
| 4,863,457 A |   | 9/1989  | Lee             |
| 4,936,825 A |   | 6/1990  | Ungerleider     |
| 5,092,837 A | * | 3/1992  | Ritch et al.    |
| 5,178,604 A |   | 1/1993  | Baerveldt et al. |
| 5,290,295 A | * | 3/1994  | Querals et al. ............. 623/1.23 |
| 5,300,020 A |   | 4/1994  | L'Esperance, Jr. |
| 5,516,522 A |   | 5/1996  | Peyman et al.   |
| 5,558,630 A |   | 9/1996  | Fisher          |
| 5,665,114 A | * | 9/1997  | Weadock et al.  |
| 5,670,161 A | * | 9/1997  | Healy et al. ................ 623/1.42 |
| 5,908,449 A | * | 6/1999  | Bruchman et al. |
| 5,932,299 A | * | 8/1999  | Katoot          |
| 5,968,058 A | * | 10/1999 | Richter et al.  |
| 6,165,210 A | * | 12/2000 | Lau et al.      |
| 6,203,513 B1 | * | 3/2001 | Yaron et al. .................... 604/9 |
| 2002/0099434 A1 | * | 7/2002 | Buscemi et al. ............ 623/1.11 |

FOREIGN PATENT DOCUMENTS

| GB | 2 296 663    |   | 7/1996 |
|----|--------------|---|--------|
| WO | 94/13234     |   | 6/1994 |
| WO | WO 94/21205  | * | 9/1994 |
| WO | 95/08310     |   | 3/1995 |

* cited by examiner

Primary Examiner—Brian L. Casler
Assistant Examiner—Catherine Serke
(74) Attorney, Agent, or Firm—Larson & Taylor PLC

(57) ABSTRACT

The present invention provides a microfistula tube including a soluble duct, defining a drainage canal having an inner surface, the duct being biocompatible, wherein the microfistula tube is coated with and/or incorporates biological for forming a basement membrane, or an intracellular matrix and a basement membrane. The biological cells may coat the inner surface of the drainage canal, and the microfistula tube may be made of a mouldable material or an absorbable material. The invention also provides an implantation system for the microfistula tube including a microfistula tube and a surgical instrument including an outer tube for penetrating body tissue, an inner tube, and an innermost rod, wherein the outer tube, the inner tube and the innermost rod are coaxial, the outer tube is adapted to receive said microfistula tube, whereby the inner tube may be used to push the microfistula tube into position and the innermost rod provides mechanical support during implantation of the microfistula tube.

75 Claims, 14 Drawing Sheets

BIOLOGICAL MICROFISTULA TUBE AND IMPLANTATION METHOD AND APPARATUS

This invention relates to a microfistula tube for the creation of microfistulae within the body, to be used for example to drain unwanted aqueous fluid, and a method and apparatus for the insertion into the body of a microfistula tube. In a preferred embodiment the microfistula tube is used for drainage of excess fluid in the eye.

Existing devices for the drainage of excessive aqueous fluid within the body, and most especially to control intraocular pressure in advanced refractory glaucoma, have been made of materials such as horse-hair, silk thread, gold foil, autologous canaliculus, tantalum wire, glass, platinum, polymethylmethacrylate, polyethylene, gelatin and autologous cartilage. Various devices made of these materials have been inserted, for example, in the anterior chamber of the eye under a conjunctival or scleral flap extending into the anterior subconjunctival space. However, problems frequently associated with existing devices include foreign-body reactions leading to fibroblast proliferation and subconjunctival fibrosis formation around the posterior exit of the drainage implant. Commonly, existing devices require large incisions of 1 mm×3 mm or even larger. Such incisions represent an extensive surgical injury and can lead to the formation of excessive quantities of scar tissue. Further, existing fistula tubes are mainly of non-biological materials and operate in far from physiological conditions. Such a fistula tube may generate an adverse tissue response, which causes blockage of the fistula tube resulting in uncontrolled eye pressure and ultimately negates any beneficial effects. More recent developments have attempted to protect the posterior exit of the drainage tube and develop posterior shunting of aqueous fluid to an equatorial sub-Tenon's collecting device.

These developments include a modified Krupin-Denver valve, the Schocket implant, the Joseph valve, and the Molteno implant.

An object of the present invention is to provide a biological microfistula tube subject to reduced rejection effects, that will lead to the formation of a microfistula for permanent or long-term aqueous fluid bypass, with minimal overdraining, and tending to impede wound healing processes and hence the closure of the drainage pathway. Further objects of the invention are to provide such a biological microfistula tube generating minimal tissue reaction, and matching outflow resistance, to allow the control of eye pressure and reduce surgical complications. A further object of the present invention is to provide a method and apparatus for the implantation of the biological microfistula tube.

According to a first broad aspect of the present invention there is provided a microfistula tube including:
 a soluble duct, defining a drainage canal having an inner surface, the duct being biocompatible, wherein
 said microfistula tube is coated with and/or incorporates biological cells for forming a basement membrane, or an intracellular matrix and a basement membrane.

Preferably the biological cells coat the inner surface of the drainage canal.

Preferably the microfistula tube is made of a mouldable material.

Preferably the microfistula tube is made of absorbable material.

Any suitable biocompatible material may be used, provided it permits the adherence of a basement membrane to the inner surface of the microfistula tube, and permits host endothelial or epithelial cells to grow in and coat the inner surface, while permitting minimal tissue reaction. Thus, the microfistula tube may be placed into a body, but will be incorporated into surrounding tissue or absorbed by the body over time. The biological cells—whose type will depend on the location where the microfistula tube is implanted—will provide a biological lining of the drainage pathway (i.e. microfistula) formed within the body by the microfistula tube, and inhibit the wound healing processes that would tend to occlude the drainage pathway. These cells will also reduce rejection effects. The biological cells, which will eventually form a permanent or long-lived endothelial, epithelial or similar lining of the drainage pathway formed by the microfistula tube minimize the tendency for fibroblast proliferation and the occlusion of the pathway. Consequently a microfistula tube size smaller than has been feasible with prior art devices or techniques may be employed, thereby reducing the risk of overdraining the aqueous fluid.

Preferably the biological cells are endothelial or trabecular meshwork cells.

Preferably the microfistula tube is made of gelatin or collagen.

By using a substance such as gelatin or collagen the mechanical and absorption properties of the tube may readily be manipulated, and the microfistula tube given the required rigidity and absorption properties.

Preferably the microfistula tube is sufficiently rigid to allow ready insertion into a living body.

Preferably the microfistula tube is a tube with a circular cross-section.

Preferably the outer surface of the microfistula tube tapers towards its forward end to facilitate its insertion into body tissues. Thus, the microfistula tube may be narrower at the forward end so that it can more easily be pushed into the relevant tissues of the body.

Preferably the duct is provided with one or more generally rearwardly projecting barbs or a generally rearwardly projecting skirt. Preferably the one or more barbs or said skirt is near the forward end of said microfistula tube. Thus, once the microfistula tube is in place it will not easily be able to move back along the path of insertion and hence be dislodged.

Preferably the rearward end of said microfistula tube has thicker walls to provide improved area and strength to allow the microfistula tube to be pushed into place by pressing against the rear end of the microfistula tube.

Preferably the rearward end of the microfistula tube has an increased outer perimeter size to prevent the microfistula tube from advancing beyond the point of implantation.

Thus, the rear end of the microfistula tube has an increased perimeter or, when the microfistula is tubular, an increased outer diameter, both to provide a broader base against which pressure may be applied to insert the microfistula tube into body tissues, and also to prevent the microfistula tube from advancing further than the point of implantation.

Preferably the microfistula tube is adapted to form a passage from the anterior chamber to Schlemm's canal, and has an interior diameter of between 100 and 200 $\mu$m, and a length of between 1 and 3 mm.

More preferably the microfistula tube has an interior diameter of approximately 150 $\mu$m and a length of approximately 2 mm.

Alternatively the microfistula tube is adapted to form a passage from the anterior chamber to the anterior subconjunctival space and has an interior diameter of between 100 and 400 μm and a length of between 2 and 6 mm.

Preferably the microfistula tube has an interior diameter of between 250 and 350 μm.

More preferably the microfistula tube has an interior diameter of approximately 300 μm and a length of approximately 3 mm.

Alternatively the microfistula tube is adapted to form a passage from the anterior chamber to the episcleral vein, with an inner diameter of between 100 and 300 μm and a length of between 7 and 14 mm.

Preferably the microfistula tube has an inner diameter of approximately 150 μm and a length of approximately 10 mm.

In one embodiment the microfistula tube is adapted to form a passage from the vitreal cavity to the subarachnoid space of the optic nerve, and has an inner diameter of between 100 and 300 μm and a length of between 3 and 12 mm.

Preferably the microfistula tube has an inner diameter of approximately 150 μm and a length of approximately 6 mm.

Thus, the microfistula tube may be used in optical applications to shunt aqueous fluid from the anterior chamber into Schlemm's canal, the subconjunctival space, or the episcleral vein, or from the vitreal cavity to the subarachnoid space of the optic nerve.

According to second broad aspect of the present invention there is provided a microfistula tube implantation system including:

a microfistula tube as described above; and a surgical instrument including an outer tube for penetrating body tissue, an inner tube, and an innermost rod, wherein said outer tube, said inner tube and said innermost rod are coaxial, said outer tube is adapted to receive said microfistula tube, whereby the inner tube may be used to push the microfistula tube into position and the innermost rod provides mechanical support during implantation of the microfistula tube.

Thus, the outer tube can be used to penetrate body tissues (for example a cornea), and the inner tube can then be used to push the microfistula tube forward and out of the forward end of the outer tube. The innermost rod may be moved with the inner tube until the microfistula tube is in its final position, and then the innermost rod may be withdrawn, followed by the inner tube. The outer tube may then be withdrawn from the body.

Preferably said microfistula tube is adapted to receive said innermost rod.

Preferably the outer tube is a hypodermic-type tube.

Preferably the inner tube is blunt-ended.

Preferably the outer tube is of stainless steel.

Preferably the inner tube is of stainless steel.

Preferably the innermost rod is of tungsten.

Preferably the surgical instrument is adapted to be attached to an ultramicrosurgical system.

Preferably the surgical instrument is adapted to be manipulated by electric motors.

Thus, the surgical instrument is adapted to deliver the microfistula tube to the required location. For greatest precision, the surgical instrument is used with a microsurgical system powered by electric motors and the operational procedures are performed under an operation microscope and gonioscopic observation.

According to third broad aspect of the present invention there is provided a microfistula tube implantation system including:

a microfistula tube as described above; and a surgical instrument including an outer tube for cutting and penetrating body tissue, and an inner rod, wherein said outer tube and said inner rod are coaxial, said outer tube is adapted to receive said microfistula tube and said inner rod, and said outer tube has a sharp forward end for cutting body tissue, whereby the outer tube may be used to create a passage to an implantation site for said microfistula tube, said inner rod may be used to position a microfistula tube at said site, and said inner rod and outer tube may be withdrawn from said site leaving said microfistula tube in position at said site.

Preferably the outer tube is a hypodermic-type tube.

Preferably the outer tube is of stainless steel.

Preferably the inner rod is of stainless steel.

Preferably the surgical instrument is adapted to be attached to an ultramicrosurgical system.

Preferably the surgical instrument is adapted to be manipulated by electric motors.

According to fourth broad aspect of the present invention there is provided a method for the implantation of a microfistula tube including:

introducing into the vicinity of a desired implantation location an implantation system as described above with said microfistula tube mounted on the innermost rod, pushing the microfistula tube out of the outer tube and into a desired location by means of the inner tube, the rod moving in unison with the inner tube and the microfistula tube, withdrawing the surgical instrument from the body.

Preferably the rod is withdrawn from the microfistula tube before the inner tube is withdrawn.

Preferably the rod and inner tube are withdrawn into the outer tube before the inner tube, outer tube and rod are withdrawn from the body.

Preferably the desired location is the anterior chamber.

According to fifth broad aspect of the present invention there is provided a method for the implantation of a microfistula tube including:

forming the passage with said outer tube of said implantation system as described above with said microfistula tube in said outer tube forward of said inner rod, advancing said microfistula tube to said implantation site with said inner rod, withdrawing said outer tube, withdrawing said inner rod, and withdrawing the surgical instrument.

Preferably the method includes withdrawing the outer tube partially, then withdrawing said inner rod partially, followed by withdrawing said inner rod and outer tube in unison.

Preferably the partial withdrawal of the outer tube continues until said forward of said outer tube is in the anterior chamber.

Preferably the method includes rotating said outer tube with a reciprocating motion while forming said passage to aid said cutting of said tissue.

BRIEF DESCRIPTION OF THE DRAWINGS

Preferred embodiments of the invention will be described, by way of example, with reference to the accompanying drawings in which.

DETAILED DESCRIPTION OF THE PREFERRED EMBODIMENTS

Figure 1:
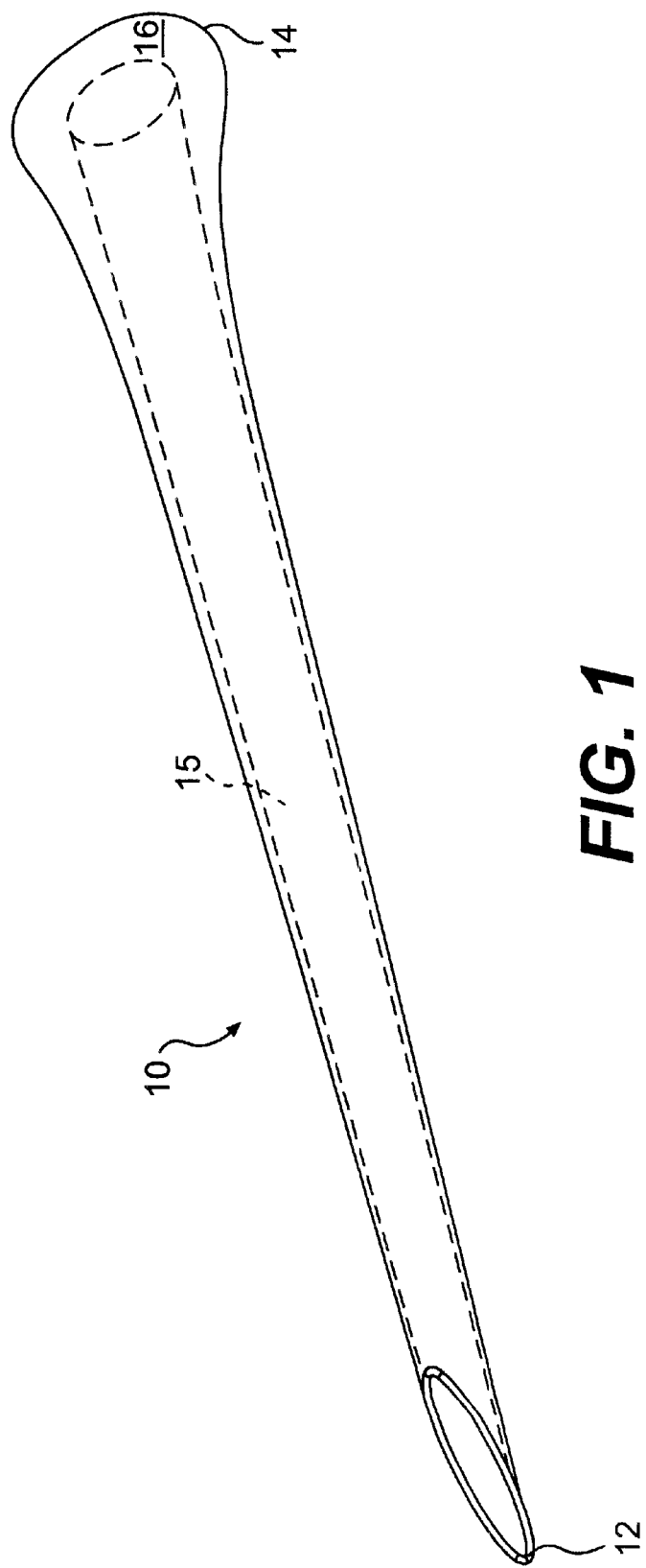
FIG. 1 is a view of a microfistula tube embodying the present invention.

A biological microfistula tube according to the present invention is shown generally at 10 in FIG. 1. The microfistula tube 10 comprises a hollow tube which defines a drainage canal 15 with a forward end 12 terminating in a point to facilitate the penetration by the microfistula tube 10 of tissue and a rear end 14. The rear end 14 of the microfistula tube 10 has thickened walls to strengthen the microfistula tube 10, as implantation of the microfistula tube 10 will generally be performed by pushing the microfistula tube 10 into place by applying pressure to the rear end 14.

The microfistula tube 10 is made from gelatin, as the mechanical and absorption properties of the gelatin can be manipulated by varying the degree of cross-linking and controlling the water content. The material can therefore be designed to have the required rigidity to withstand the implantation process, but be absorbed after a controllable period. In most instances this would be only a matter of days or weeks.

The microfistula tube incorporates biological cells. Such cells lead to the formation of a biological lining of the drainage canal, which inhibits the wound-healing processes that would tend to occlude the drainage pathway. These cells (not shown) are either endothelial cells or ocular trabecular meshwork cells. These cells would generally line the inner surface of the microfistula tube 10, though other configurations are possible, such as incorporating the cells into the material of the microfistula tube 10.

Optionally, the microfistula tube 10 can be provided with one or more rearward pointing barbs (not shown), preferably located near the forward end 12 and on the outer surface of the microfistula tube 10. These barbs would resist the unwanted rearward movement of the microfistula tube 10 following implantation. The flared rear end 14 of the microfistula tube 10, and the generally tapered profile of the microfistula tube 10, will resist unwanted forward movement of the microfistula tube 10. The thickening of the rear end 14 of the microfistula tube 10 can be extended forward some distance to further resist unwanted forward motion of the microfistula tube 10 after implantation. This thickened portion of the rearward end 14 may be terminated more abruptly than shown in FIG. 1, so that a substantially forward facing surface is provided for this purpose. Finally, the rearward pointing face 16 of the rear end 14 of the microfistula tube 10 may be recessed or otherwise adapted to receive the forward end of a surgical instrument, to facilitate implantation of the microfistula tube 10 by means of such an instrument.

Figure 2:
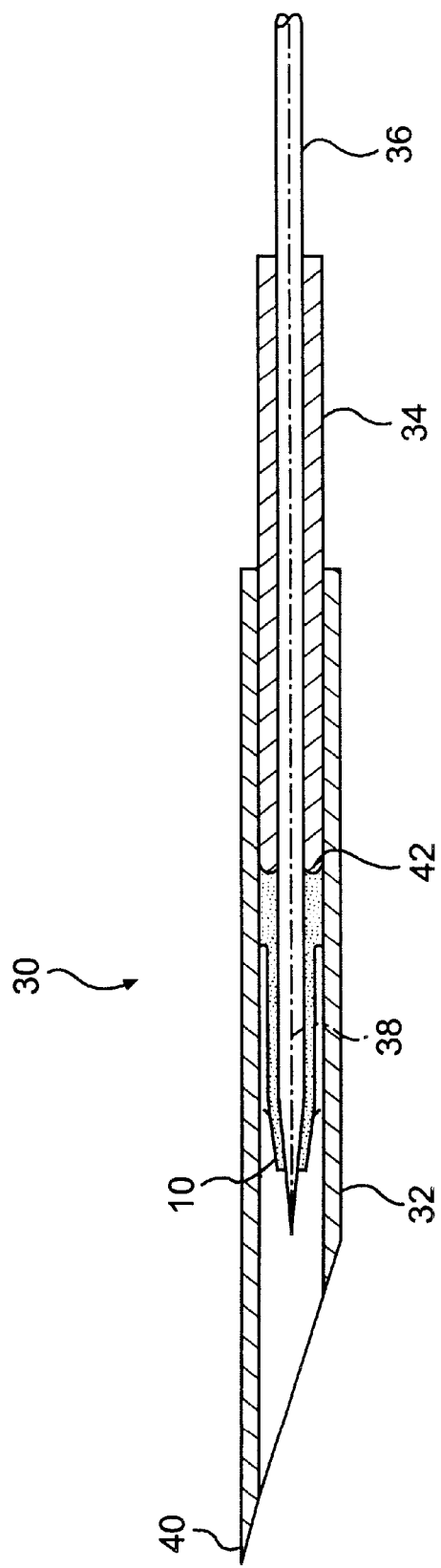
FIG. 2 is a view of a microfistula tube and surgical instrument according to a further embodiment of the present invention.
Figure 3:
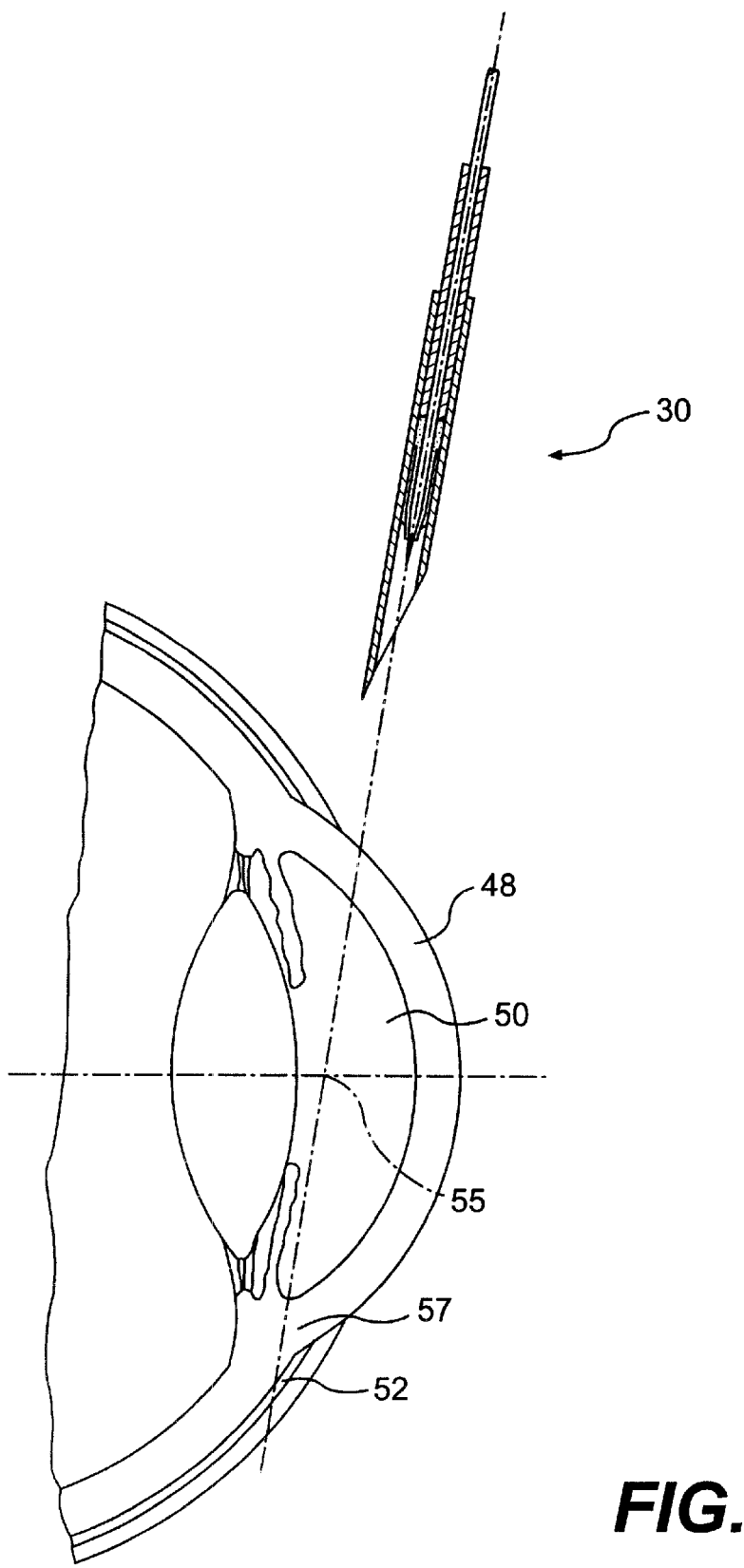
FIG. 3 illustrates a method for the implantation of a microfistula tube according to a further embodiment of the present invention.

A surgical instrument according to the present invention provided with a microfistula tube 10 is shown generally at 30 in FIG. 2. The surgical instrument 30 shown in the Figure is adapted for the implantation of the microfistula tube 10 into the eye to form a drainage pathway from the anterior chamber to the subconjunctival space. The microfistula tube 10 shown in the Figure includes rearward pointing barbs and a recessed base, as discussed above. The surgical instrument 30 comprises an outer tube 32 in the form of a hypodermic-type stainless steel tube, an inner tube 34 in the form of a blunt-ended stainless steel tube, and an innermost rod 36 made of tungsten. The microfistula tube 10 is shown located around the forward end 38 of the innermost rod 36. The innermost rod 36 may slide within the inner tube 34, and the inner tube 34 may slide within the outer tube 32.

The outer tube 32 is adapted to penetrate the cornea, while the inner tube 34 is adapted to push the microfistula tube 10 from the outer tube 32 and into its final position. The innermost rod 36 is adapted to provide mechanical support during the implantation of the microfistula tube 10.

In use, the surgical instrument 30 would be attached to and manipulated by means of an ultramicrosurgical system, and the operation performed under an operation microscope and gonioscopic observation. All movement would be produced by electric motor.

It should be noted that the outer tube 32 is sharp at its forward end 40 to facilitate the penetration of the cornea. The inner tube 34 is rounded at its forward end 42, and the rear end of the microfistula tube 10 has a corresponding recess, so that the end 42 of the inner tube 34 may be received by the base of the microfistula tube 10.

A surgical implantation method according to the present invention is illustrated in FIGS. 3 to 8. The method illustrated in these figures is for the implantation of a microfistula tube to form a passage, by way of the drainage canal 15, between the anterior chamber 50 (see FIGS. 3 to 8) and the anterior subconjunctival space 52 (see FIGS. 3 to 8). The entry point is 2 mm anterior to the limbus on the temporal side (see FIG. 3). This entry point may also be a pivot point of an ultramicrosurgical system, if such a system is used to manipulate the surgical instrument.

Figure 4:
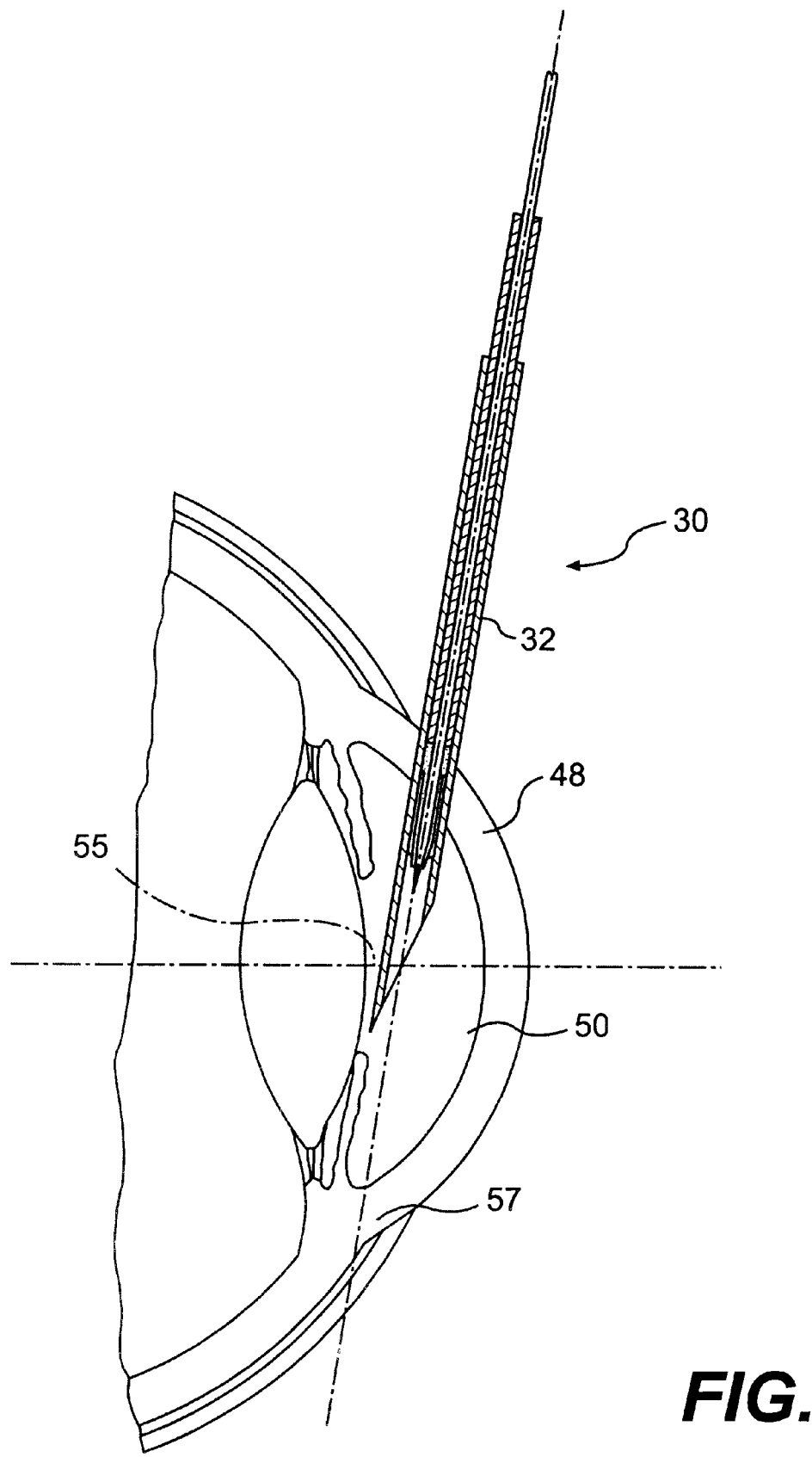
FIG. 4 is a further illustration of the method for the implantation of a microfistula tube shown in FIG. 3, wherein a surgical instrument and microfistula tube are shown having penetrated a cornea.

The surgical instrument 30 provided with a microfistula tube 10 penetrates the cornea 48, and enters the anterior chamber 50 (see FIG. 4). The insertion of the surgical instrument 30 continues until the outer tube 32 of the surgical instrument 30 reaches the centre of the pupil 55.

Figure 7:
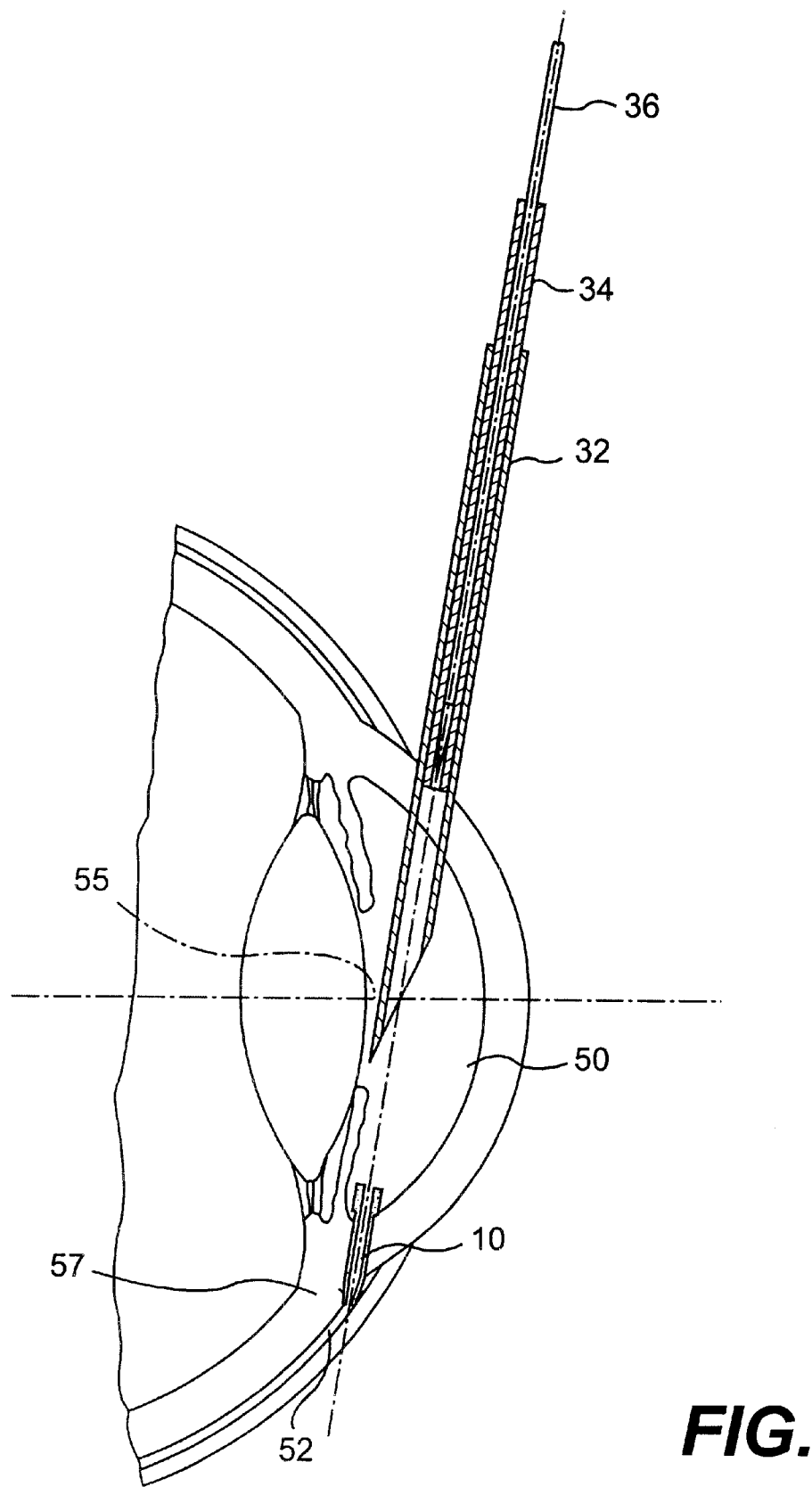
FIG. 7 is a further illustration of the method of FIG. 3, in which the inner tube and supporting rod are shown retracted into the outer hypodermic-type tube.

The inner tube 34, the innermost rod 36, and the microfistula tube 10 are advanced further (see FIG. 5), until the innermost rod 36 with the microfistula tube 10 penetrates the trabecular meshwork and sclera 57 until the tip of the microfistula tube 10 reaches the subconjunctival space 52. The innermost rod 36 is then withdrawn from the microfistula tube 10 (FIG. 6), and the innermost rod (now withdrawn into the inner tube 34) and the inner tube 34 are retracted into the outer tube 32 (FIG. 7).

Figure 8:
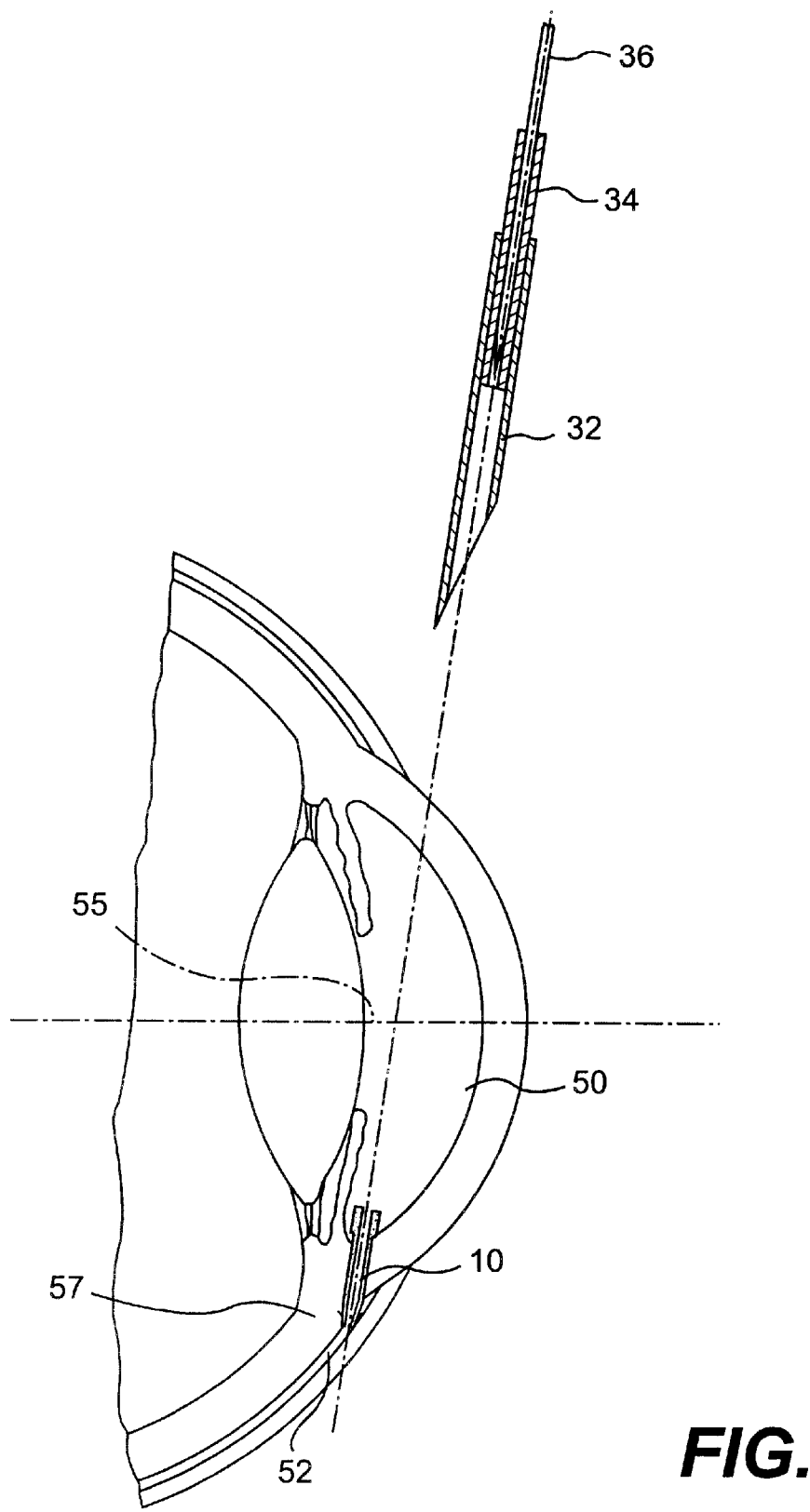
FIG. 8 is a further illustration of the method of FIG. 3, in which the completed method is shown with the microfistula tube implanted in the eye and the surgical instrument removed from the cornea.

Finally, the surgical instrument 30 is withdrawn from the eye, leaving the implanted microfistula tube 10 in position (FIG. 8). In practice, a suture would generally then be placed to close the corneal wound.

In this procedure, the microfistula tube 10 has an inner diameter of 100 μm and a length of 3 mm. In alternative embodiments, the microfistula tube 10 can be implanted to form a passage between the anterior chamber and Schlemm's canal, in which case the inner diameter of the microfistula tube 10 is 150 μm and its length is 2 mm. In another embodiment the microfistula tube 10 forms a passage between the anterior chamber and the episcleral vein, and has an inner diameter of 150 μm and a length of 10 mm. Alternatively, a microfistula tube of inner diameter 150 μm and length 6 mm may be used to form a passage from the vitreal cavity to subarachnoid space of the optic nerve.

Figure 5:
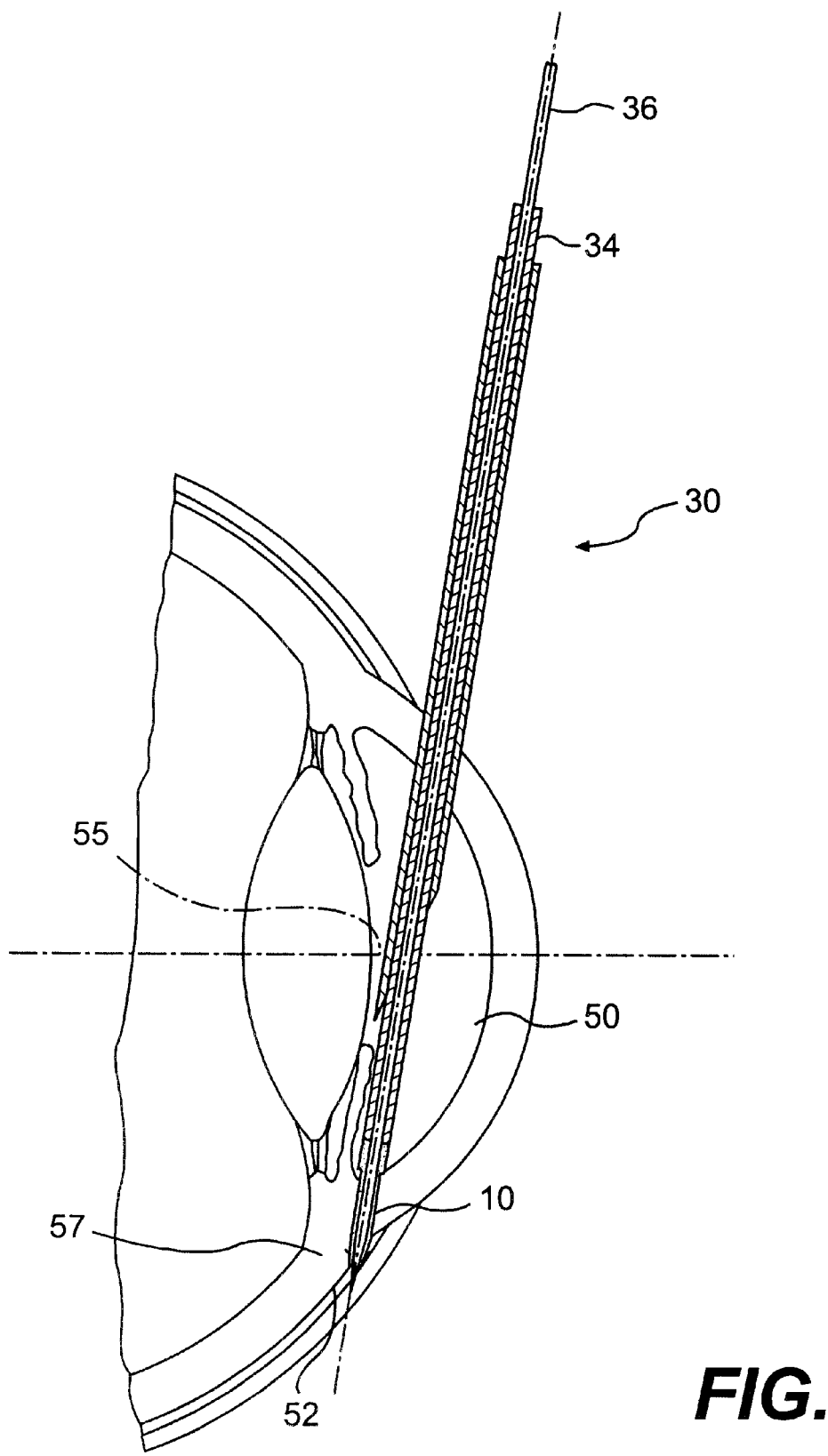
FIG. 5 shows a further stage in the method of FIG. 3, in which a microfistula tube has been moved into its final position in the eye.
Figure 6:
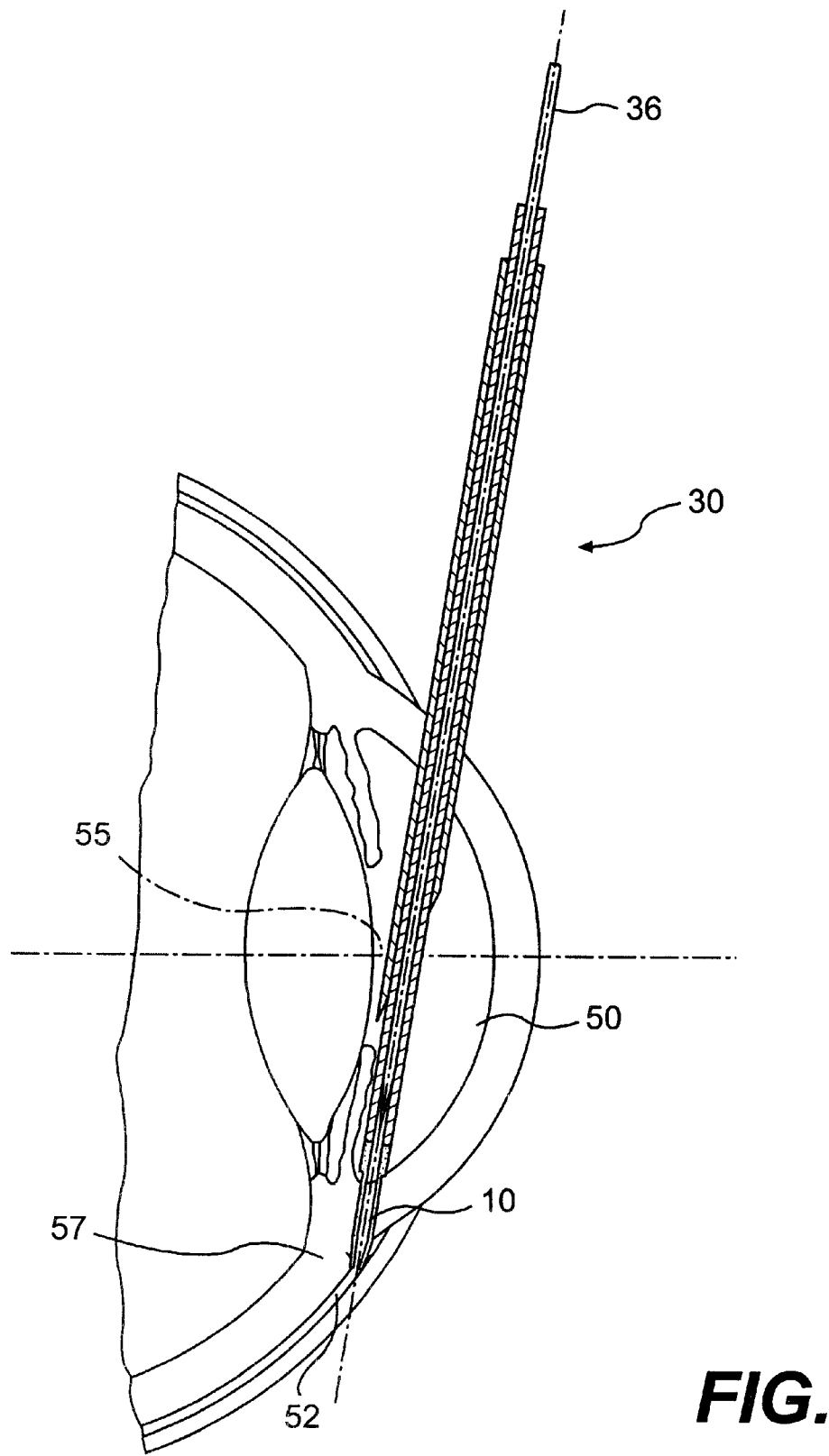
FIG. 6 shows a further illustration of the method of FIG. 3, in which the supporting rod is shown withdrawn from the microfistula tube.
Figure 9:
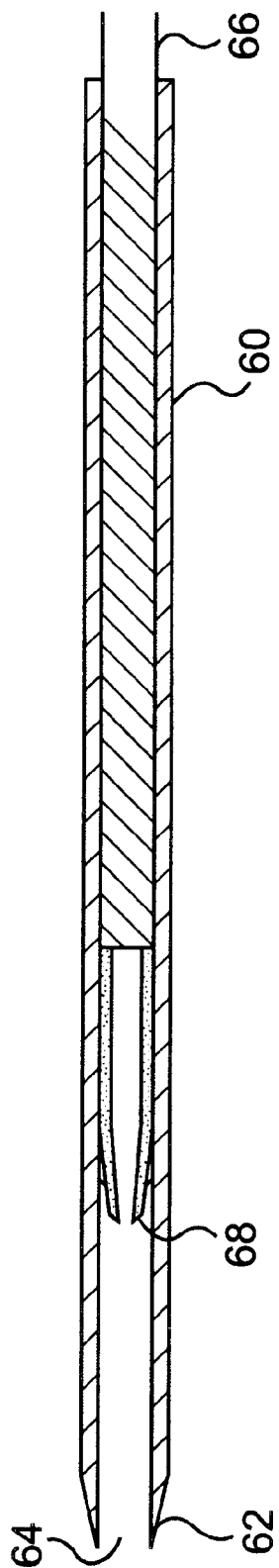
FIG. 9 is a view of a surgical instrument and microfistula tube according to a further embodiment of the present invention.

In some embodiments of the present invention, when the inner tube 34, the innermost rod 36, and the microfistula tube 10 are advanced as shown in FIG. 5, the resistance to penetration of the surrounding tissues may be so high that the microfistula tube cannot penetrate these tissues and collapses under the force of the inner tube 34. It may be preferable, therefore, to provide the outer tube at its forward end with a sharp end for cutting through the surrounding tissue. Referring to FIG. 9, which is a view of an alternative embodiment of the implantation system of the present invention, outer tube 60 is again a hypodermic-type stainless steel tube. Unlike outer tube 32 of the embodiment illustrated in FIG. 2, however, the forward end 62 of outer tube 60 is sharpened and the opening 64 at the forward end 62 faces forwardly rather than obliquely. Stainless steel inner rod 66 is provided within outer tube 60 and microfistula tube 68 is positioned forward of inner rod 66. Microfistula tube 68 will generally be substantially identical to those described above, but may lack the reinforced base of the above embodiments.

Figure 10:
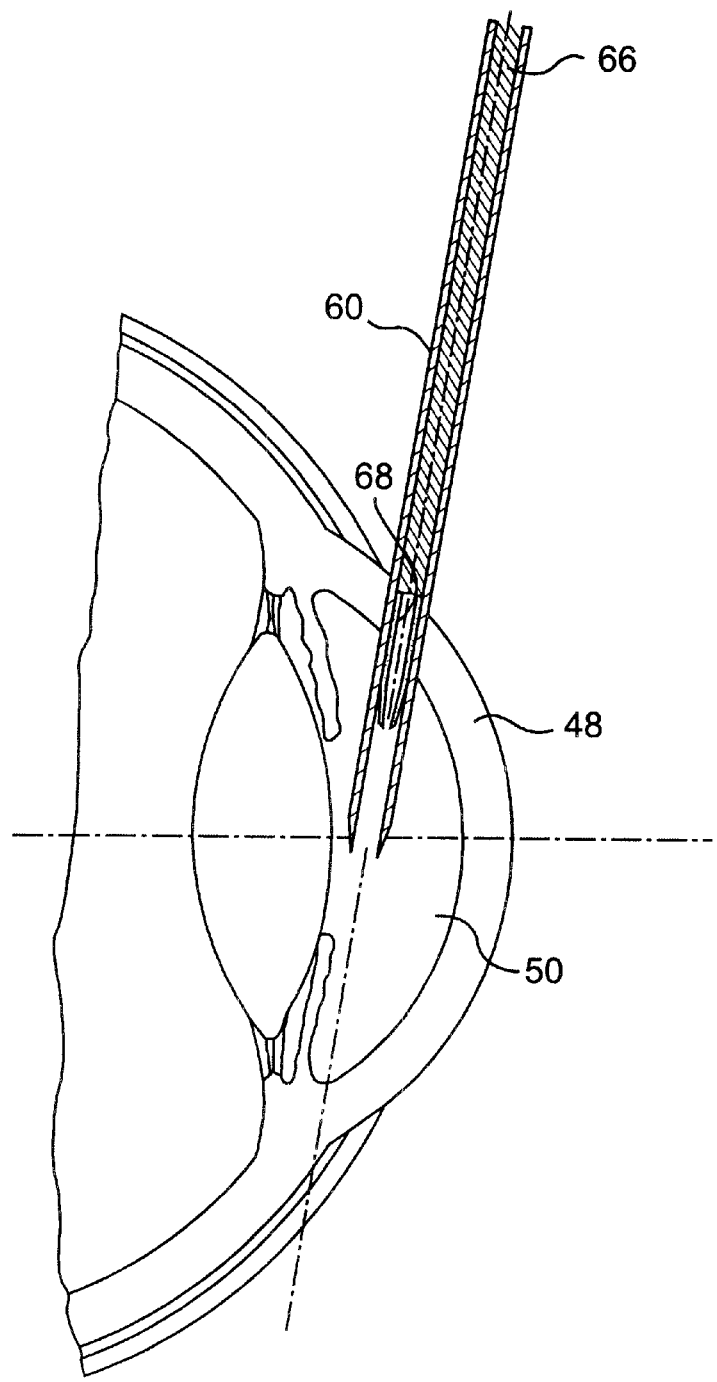
FIG. 10 is a view of a method of implantation of the microfistula tube by means of the surgical instrument of FIG. 9, wherein the surgical instrument and microfistula tube are shown having penetrated a cornea.
Figure 11:
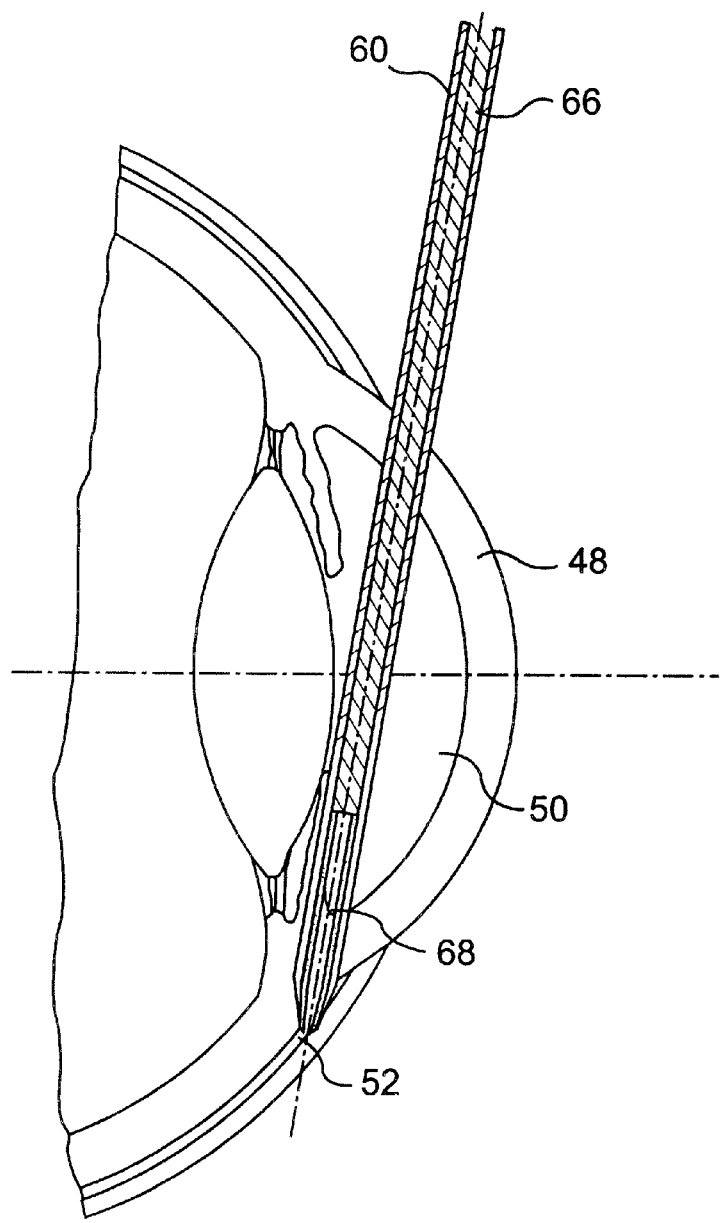
FIG. 11 shows a further stage in the method of FIG. 10, in which the surgical instrument has been advanced to the subconjunctival space.

A method of implantation of a microfistula tube by means of this embodiment of the surgical instrument is illustrated in FIGS. 10 to 14. The method illustrated in these figures is again for the implantation of a microfistula tube between the anterior chamber and the anterior subconjunctival space. Referring to FIG. 10, outer tube 60 is preferably rotated to assist the cutting of body tissues. This rotation alternates rapidly in direction so that tissue is cut by the tube 60. The outer tube 60 penetrates the cornea 48, and enters the anterior chamber 50. Inner rod 66 is not rotated during this insertion of the instrument or subsequently. Inner rod 66 and microfistula tube 68 are advanced with outer tube 60 until the forward end 62 of outer tube 60 reaches subconjunctival space 52 (see FIG. 11).

Figure 12:
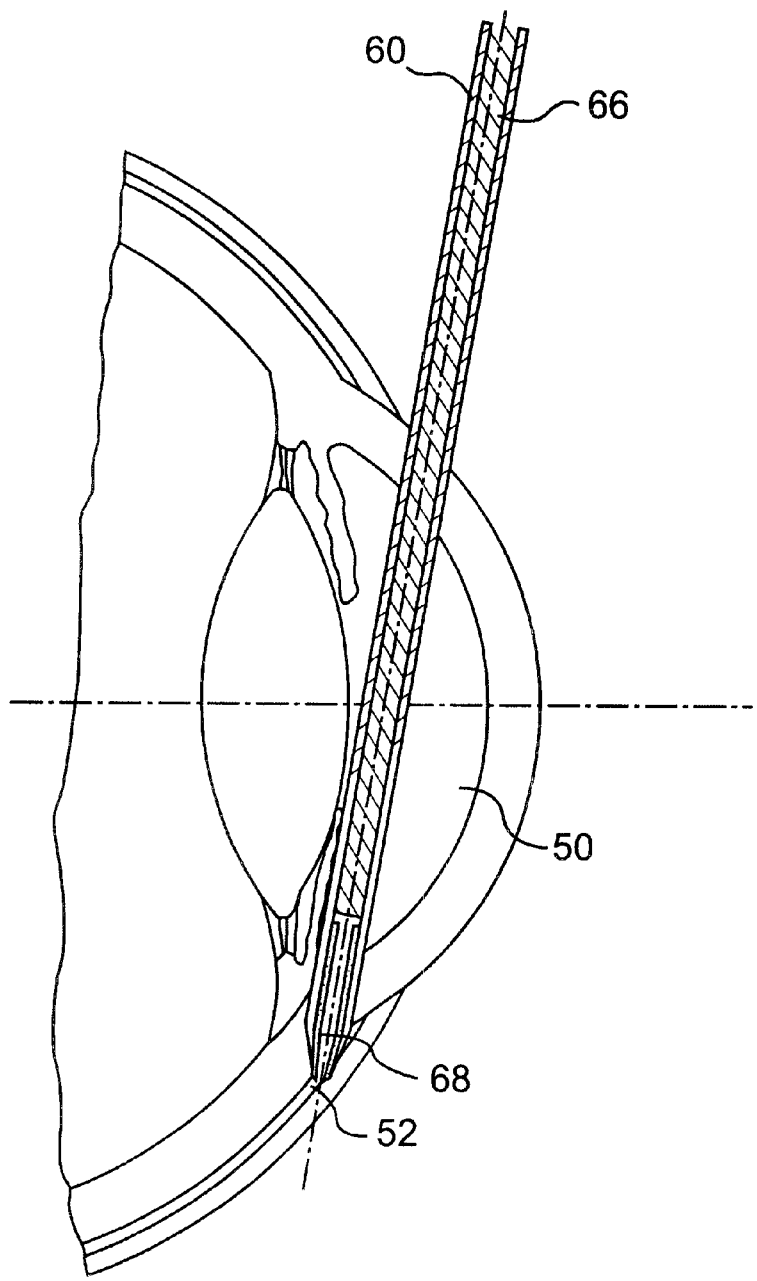
FIG. 12 shows a further illustration of the method of FIG. 10, in which the microfistula tube has been advanced to an implantation site.
Figure 13:
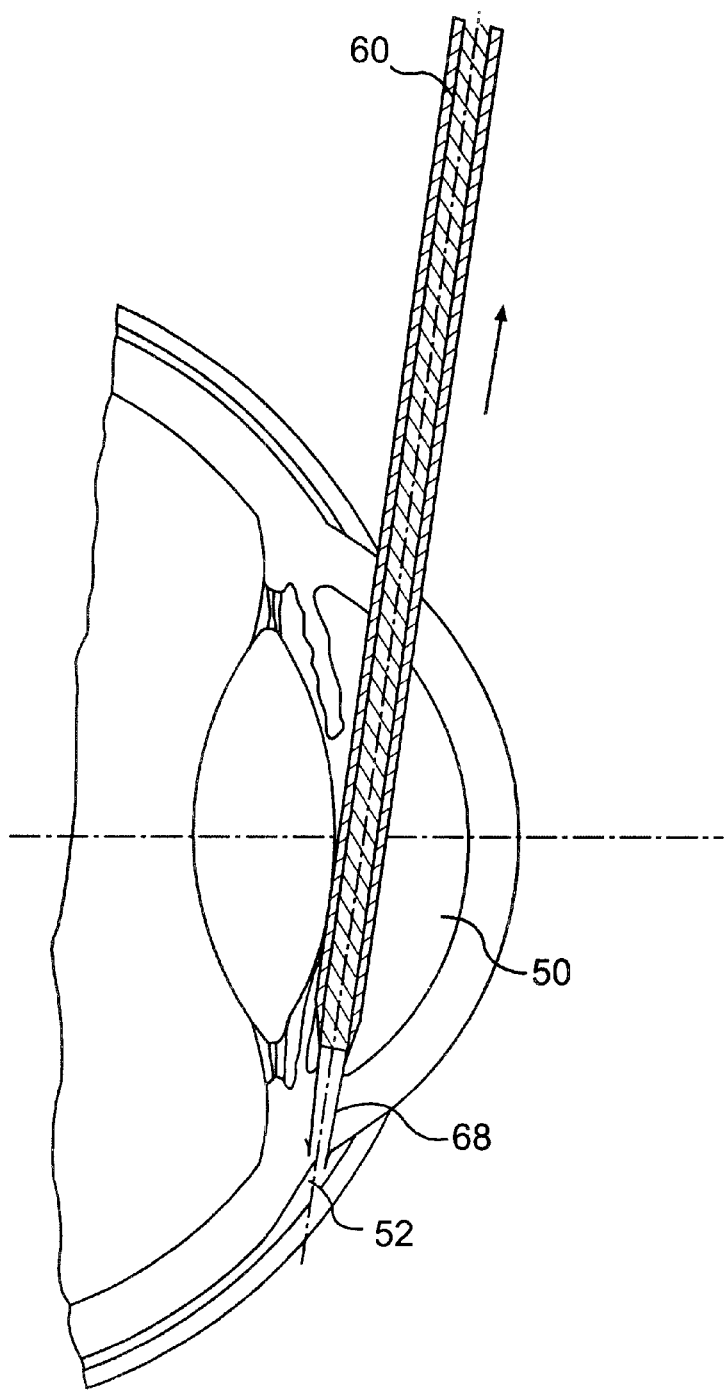
FIG. 13 is a further illustration of the method of FIG. 10, in which the outer tube of the surgical instrument has been withdrawn to the anterior space.
Figure 14:
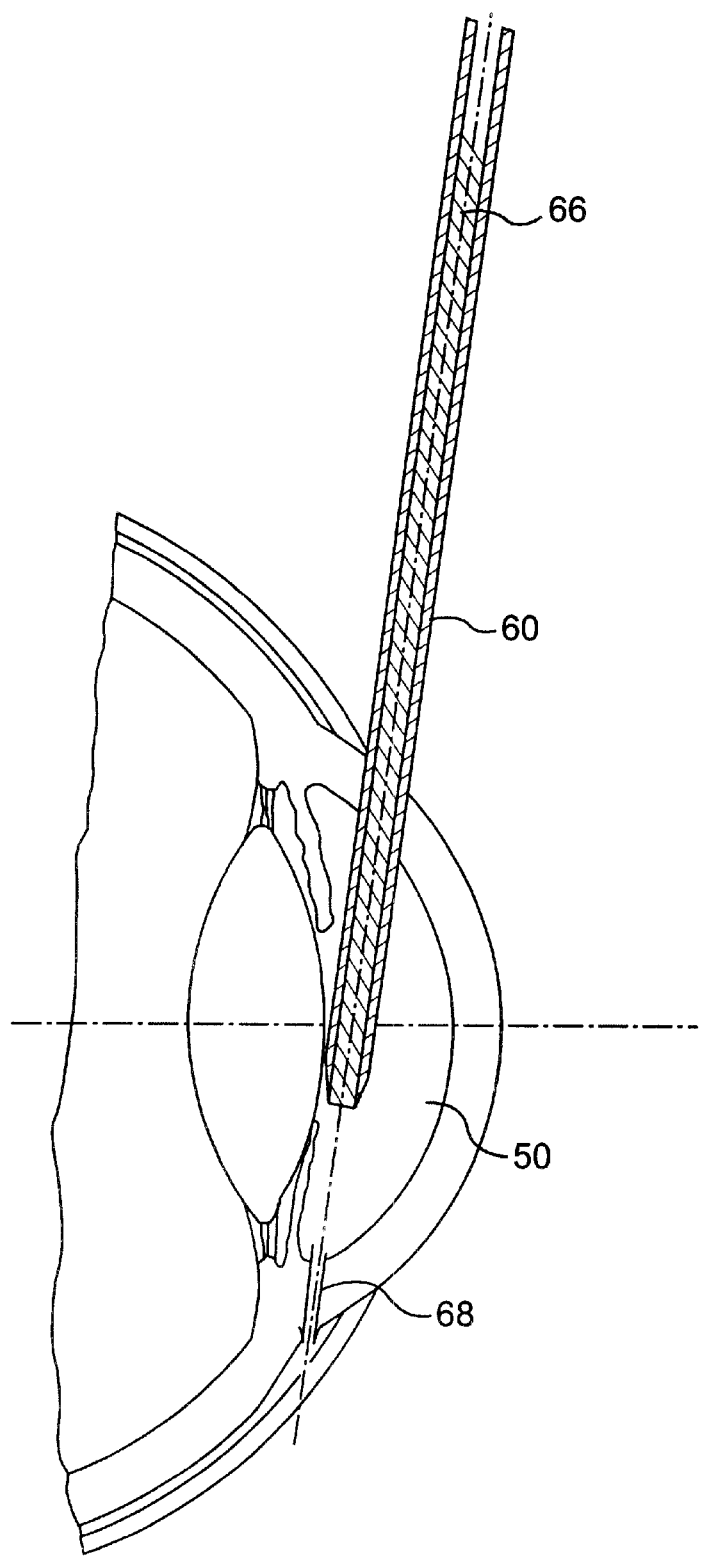
FIG. 14 is a further illustration of the method of FIG. 10, in which the nearly completed method is shown with the microfistula tube implanted in the eye and the surgical instrument withdrawn to the anterior space.

Referring to FIG. 12, the inner rod 66 is then advanced within outer tube 60, propelling microfistula tube 68 forward until microfistula tube 68 is adjacent to or extending marginally beyond the end 62 of outer tube 60. Referring to FIG. 13, outer tube 60 is withdrawn from the immediate vicinity of the subconjunctival space 52, with inner rod 66 held stationary, until microfistula tube 68 is entirely released from the outer tube 60. The inner rod 66 prevents outer tube 60 from withdrawing the microfistula tube 68 during this step, after the completion of which the forward end 62 of outer tube 60 is in the anterior chamber 50.

Finally, the outer tube 60 and inner rod 66 (see FIG. 14) are withdrawn from the body together, leaving the microfistula tube 68 at the implantation site.

Modifications within the spirit and scope of the invention may readily be effected by persons skilled in the art. For example, microfistula tubes may be adapted for use in other parts of the body where there is obstructed flow of fluid and/or high fluid pressure, with appropriate dimensions and corresponding surgical instrumentation. Possible other sites include the cranium (to treat raised intracranial pressure), shunting from the subarachnoid space to one of the head or neck veins, incorporating in the microfistula tube a material favouring the growth of venous or subarachnoid space endothelial cells, or—in the treatment of Menière's Disease—the invention may be used to shunt from endolymph to perilymph in the inner ear using a material favourable to the growth of subarachnoid endothelial cells. Further, such biological microfistula tubes may be useful in surgery upon the ureter or urethra, to overcome obstructions or strictures, using material favourable to the growth of urogenital epithelial cells. In addition, although the surgical instrument described above has been designed for the implantation of microfistula tubes, it may also be adapted for use for the implantation of other surgical or medical devices. Consequently, it is to be understood that this invention is not limited to the particular embodiments described by way of example hereinabove.

What is claimed is:

1. A microfistula tube comprising:
   a biocompatible, soluble tube defining a drainage canal having an inner surface and, when said soluble tube is disposed in the body of a patient, said soluble tube is functional as a drainage tube and will eventually fully dissolve and be absorbed by the body; and
   biological cells for forming a basement membrane or for forming an intracellular matrix and a basement membrane;
   wherein said soluble tube is coated with said biological cells, incorporates said biological cells or both incorporates and is coated with said biological cells, and wherein said microfistula tube is made of absorbable material.

2. The microfistula tube as claimed in claim 1 wherein the biological cells coat the inner surface of the drainage canal.

3. The microfistula tube as claimed in claim 1 wherein the microfistula tube is made of a mouldable material.

4. The microfistula tube as claimed in claim 1 wherein the biological cells are endothelial or trabecular meshwork cells.

5. The microfistula tube as claimed in claim 1 wherein the microfistula tube is made of gelatin or collagen.

6. The microfistula tube as claimed in claim 1 wherein the microfistula tube is sufficiently rigid to allow ready insertion into a living body.

7. The microfistula tube as claimed in claim 1 wherein the circumferential outer surface of the microfistula tube tapers towards its forward end to facilitate its insertion into body tissues.

8. The microfistula tube as claimed in claim 1 wherein the soluble tube is provided with one or more generally rearwardly projecting barbs or a generally rearwardly projecting skirt.

9. The microfistula tube as claimed in claim 8 wherein said one or more barbs or said skirt is near the forward end of said microfistula tube.

10. The microfistula tube as claimed in claim 1 wherein the microfistula tube is adapted to form a passage from the anterior chamber to Schlemm's canal, and has an interior diameter of between 100 and 200 µm, and a length of between 1 and 3 mm.

11. The microfistula, tube as claimed in claim 10 wherein the microfistula tube has an interior diameter of approximately 150 µm and a length of approximately 2 mm.

12. The microfistula tube as claimed in claim 1 wherein the microfistula tube is adapted to form a passage from the anterior chamber to the anterior subconjunctival space and has an interior diameter of between 100 and 400 µm and a length of between 2 and 6 mm.

13. The microfistula tube as claimed in claim 12 wherein the microfistula tube has an interior diameter of between 250 and 350 µm.

14. The microfistula tube as claimed in claim 12 wherein the microfistula tube has an interior diameter of approximately 300 µm and a length of approximately 3 mm.

15. The microfistula tube as claimed in claim 1 wherein the microfistula tube is adapted to form a passage from the anterior chamber to the episcleral vein, with an inner diameter of between 100 and 300 µm and a length of between 7 and 14 mm.

16. The microfistula tube as claimed in claim 15 wherein the microfistula tube has an inner diameter of approximately 150 µm and a length of approximately 10 mm.

17. The microfistula tube as claimed in claim 1 wherein the microfistula tube is adapted to form a passage from the vitreal cavity to the subarachnoid space of the optic nerve, and has an inner diameter of between 100 and 300 µm and a length of between 3 and 12 mm.

18. The microfistula tube as claimed in claim 17 wherein the microfistula tube has an inner diameter of approximately 150 µm. and a length of approximately 6 mm.

19. A microfistula tube implantation system comprising:
the microfistula tube as claimed in claim 1; and
a surgical instrument including an outer tube for penetrating body tissue,
an inner tube, and an innermost rod,
wherein said outer tube, said inner tube and said innermost rod are coaxial, said outer tube is adapted to receive said microfistula tube, whereby the inner tube may be used to push the microfistula tube into position and the innermost rod provides mechanical support during implantation of the microfistula tube.

20. The microfistula tube implantation system as claimed in claim 19, wherein said microfistula tube is adapted to receive said innermost rod.

21. The microfistula tube implantation system as claimed in claim 19 wherein the outer tube is a hypodermic-type tube.

22. The microfistula tube implantation system as claimed in claim 19 wherein the inner tube is blunt-ended.

23. The microfistula tube implantation system as claimed in claim 19 wherein the innermost rod is of tungsten.

24. The microfistula tube implantation system as claimed in claim 19 wherein the surgical instrument is adapted to be attached to an ultramicrosurgical system.

25. The microfistula tube implantation system as claimed in claim 19 wherein the surgical instrument is adapted to be manipulated by electric motors.

26. A method for the implantation of a microfistula tube comprising:
introducing into the vicinity of a desired implantation location the implantation system as claimed in claim 19 with said microfistula tube mounted on the innermost rod,
pushing the microfistula tube out of the outer tube and into a desired location by means of the inner tube, the rod moving in unison with the inner tube and the microfistula tube,
withdrawing the surgical instrument from the body.

27. The method as claimed in claim 26 wherein the rod is withdrawn from the microfistula tube before the inner tube is withdrawn.

28. The method as claimed in claim 26 wherein the rod and inner tube are withdrawn into the outer tube before the inner tube, outer tube and rod are withdrawn from the body.

29. The method as claimed in claim 26 wherein the desired location is the anterior chamber.

30. A microfistula tube implantation system comprising:
the microfistula tube as claimed in claim 1; and
a surgical instrument including an outer tube for cutting and penetrating body tissue, and
an inner rod,
wherein said outer tube and said inner rod are coaxial, said outer tube is adapted to receive said microfistula tube and said inner rod, and said outer tube has a sharp forward end for cutting body tissue, whereby the outer tube may be used to create a passage to an implantation site for said microfistula tube, said inner rod may be used to position a microfistula tube at said site, and said inner rod and outer tube may be withdrawn from said site leaving said microfistula tube in position at said site.

31. A method for the implantation of a microfistula tube comprising:
forming a passage with a outer tube of the implantation system as claimed in claim 30 with said microfistula tube in said outer tube forward of said inner rod,
advancing said microfistula tube to said implantation site with said inner rod,
withdrawing said outer tube,
withdrawing said inner rod, and
withdrawing the surgical instrument.

32. The method as claimed in claim 31 including withdrawing the outer tube partially, then withdrawing said inner rod partially, followed by withdrawing said inner rod and outer tube in unison.

33. The method as claimed in claim 32 wherein said partial withdrawal of the outer tube continues until said forward of said outer tube is in the anterior chamber.

34. The method as claimed in claim 31 including rotating said outer tube while forming said passage to aid said cutting of said tissue.

35. A microfistula tube comprising:
a biocompatible, soluble tube defining a drainage canal having an inner surface; and
biological cells for forming a basement membrane or for forming an intracellular matrix and a basement membrane;

wherein said soluble tube is coated with said biological cells, incorporates said biological cells or both incorporates and is coated with said biological cells, and wherein said soluble tube is made of gelatin or collagen wherein said microfistula tube has a rearward end having thicker walls to provide improved area and strength to allow the microfistula tube to be pushed into place by pressing against the rearward end of the microfistula tube.

36. The microfistula tube as claimed in claim 35 wherein the biological cells are endothelial or trabecular meshwork cells.

37. The microfistula tube as claimed in claim 35 wherein the microfistula tube is sufficiently rigid to allow ready insertion into a living body.

38. A microfistula tube comprising:
a biocompatible, soluble tube defining a drainage canal having an inner surface and, when said soluble tube is disposed in the body of a patient, said soluble tube is functional as a drainage tube and will eventually fully dissolve and be absorbed by the body; and
biological cells for forming a basement membrane or for forming an intracellular matrix and a basement membrane;
wherein said soluble tube is coated with said biological cells, incorporates said biological cells or both incorporates and is coated with said biological cells, and said soluble tube is provided with one or more generally rearwardly projecting barbs or a generally rearwardly projecting skirt.

39. The microfistula tube as claimed in claim 38 wherein the biological cells coat the inner surface of the drainage canal.

40. The microfistula tube as claimed in claim 38 wherein the microfistula tube is made of a mouldable material.

41. The microfistula tube as claimed in claim 38 wherein the biological cells are endothelial or trabecular meshwork cells.

42. The microfistula tube as claimed in claim 38 wherein the soluble tube is made of gelatin or collagen.

43. The microfistula tube as claimed in claim 38 wherein the microfistula tube is sufficiently rigid to allow ready insertion into a living body.

44. The microfistula tube as claimed in claim 38 wherein the circumferential outer surface of the microfistula tube tapers towards its forward end to facilitate its insertion into body tissues.

45. The microfistula tube as claimed in claim 38 wherein said one or more barbs or said skirt is near the forward end of said microfistula tube.

46. The microfistula tube as claimed in claim 38 wherein said microfistula tube has a rearward end having thicker walls to provide improved area and strength to allow the microfistula tube to be pushed into place by pressing against the rearward end of the microfistula tube.

47. The microfistula tube as claimed in claim 38 wherein the microfistula tube has a rearward end having an increased outer perimeter size to prevent the microfistula tube from advancing beyond the point of implantation.

48. The microfistula tube as claimed in claim 38 wherein the microfistula tube is adapted to form a passage from the anterior chamber to Schlemm's canal, and has an interior diameter of between 100 and 200 $\mu$m, and a length of between 1 and 3 mm.

49. The microfistula tube as claimed in claim 48 wherein the microfistula tube has an interior diameter of approximately 150 $\mu$m and a length of approximately 2 mm.

50. The microfistula tube as claimed in claim 38 wherein the microfistula tube is adapted to form a passage from the anterior chamber to the anterior subconjunctival space and has an interior diameter of between 100 and 400 $\mu$m and a length of between 2 and 6 mm.

51. The microfistula tube as claimed in claim 50 wherein the microfistula tube has an interior diameter of between 250 and 350 $\mu$m.

52. The microfistula tube as claimed in claim 50 wherein the microfistula tube has an interior diameter of approximately 300 $\mu$m and a length of approximately 3 mm.

53. The microfistula tube as claimed in claim 38 wherein the microfistula tube is adapted to form a passage from the anterior chamber to the episcleral vein, with an inner diameter of between 100 and 300 $\mu$m and a length of between 7 and 14 mm.

54. The microfistula tube as claimed in claim 53 wherein the microfistula tube has an inner diameter of approximately 150 $\mu$m and a length of approximately 10 mm.

55. The microfistula tube as claimed in claim 38 wherein the microfistula tube is adapted to form a passage from the vitreal cavity to the subarachnoid space of the optic nerve, and has an inner diameter of between 100 and 300 $\mu$ and a length of between 3 and 12 mm.

56. The microfistula tube as claimed in claim 55 wherein the microfistula tube has an inner diameter of approximately 150 $\mu$m and a length of approximately 6 mm.

57. A microfistula tube implantation system comprising:
a microfistula tube comprising a biocompatible, soluble tube defining a drainage canal having an inner surface, and biological cells for forming a basement membrane or for forming an intracellular matrix and a basement membrane, wherein said soluble tube is coated with said biological cells, incorporates said biological cells or both incorporates and is coated with said biological cells; and
a surgical instrument including an outer tube for penetrating body tissue, an inner tube, and an innermost rod, wherein said outer tube, said inner tube and said innermost rod are coaxial, said outer tube is adapted to receive said microfistula tube, whereby the inner tube may be used to push the microfistula tube into position and the innermost rod provides mechanical support during implantation of the microfistula tube, and said outer tube is a hypodermic-type tube.

58. The microfistula tube implantation system as claimed in claim 57, wherein said microfistula tube is adapted to receive said innermost rod.

59. The microfistula tube implantation system as claimed in claim 57 wherein the inner tube is blunt-ended.

60. The microfistula tube implantation system as claimed in claim 57 wherein the innermost rod is of tungsten.

61. The microfistula tube implantation system as claimed in claim 57 wherein the surgical instrument is adapted to be attached to an ultramicrosurgical system.

62. The microfistula tube implantation system as claimed in claim 57 wherein the surgical instrument is adapted to be manipulated by electric motors.

63. A microfistula tube implantation system comprising:
a microfistula tube comprising a biocompatible, soluble tube defining a drainage canal having an inner surface and, when said soluble tube is disposed in the body of a patient, said soluble tube is functional as a drainage tube and will eventually fully dissolve and be absorbed by the body, and biological cells for forming a basement membrane or for forming an intracellular matrix and a basement membrane, wherein said soluble tube is coated with said biological cells, incorporates said biological cells or both incorporates and is coated with said biological cells; and wherein said microfistula tube has a rearward end having thicker walls to provide improved area and strength to allow the microfistula tube to be pushed into place by pressing against the rearward end of the microfistula tube, a surgical instrument including an outer tube for cutting and penetrating body tissue, and an inner rod, wherein said outer tube and said inner rod are coaxial, said outer tube is adapted to receive said microfistula tube and said inner rod, and said outer tube has a sharp forward end for cutting body tissue, whereby the outer tube may be used to create a passage to an implantation site for said microfistula tube, said inner rod may be used to position a microfistula tube at said site, and said inner rod and outer tube may be withdrawn from said site leaving said microfistula tube in position at said site.

64. A method for the implantation of a microfistula tube comprising:
1) introducing into the vicinity of a desired implantation location a microfistula tube implantation system comprising:
   a microfistula tube comprising a biocompatible, soluble tube defining a drainage canal having an inner surface, and biological cells for forming a basement membrane or for forming an intracellular matrix and a basement membrane, wherein said soluble tube is coated with said biological cells, incorporates said biological cells or both incorporates and is coated with said biological cells; and
   a surgical instrument including an outer tube for penetrating body tissue, and inner tube, and an innermost rod, wherein said outer tube, said inner tube and said innermost rod are coaxial, said outer tube is adapted to receive said microfistula tube, whereby the inner tube may be used to push the microfistula tube into position and the innermost rod provides mechanical support during implantation of the microfistula tube;
2) mounting said microfistula tube on the innermost rod;
3) pushing the microfistula tube out of the outer tube and into a desired location by means of the inner tube, the rod moving in unison with the inner tube and the microfistula tube; and
4) withdrawing the surgical instrument from the body;
wherein said rod is withdrawn from the microfistula tube before said inner tube is withdrawn.

65. The method as claimed in claim 64 wherein the rod and inner tube are withdrawn into the outer tube before the inner tube, outer tube and rod are withdrawn from the body.

66. The method as claimed in claim 64 wherein the desired location is the anterior chamber.

67. A method for the implantation of a microfistula tube comprising:
1) introducing into the vicinity of a desired implantation location a microfistula tube implantation system comprising:
   a microfistula tube comprising a biocompatible, soluble tube defining a drainage canal having an inner surface, and biological cells for forming a basement membrane or for forming an intracellular matrix and a basement membrane, wherein said soluble tube is coated with said biological cells, incorporates said biological cells or both incorporates and is coated with said biological cells; and
   a surgical instrument including an outer tube for penetrating body tissue, an inner tube, and an innermost rod, wherein said outer tube, said inner tube and said innermost rod are coaxial, said outer tube is adapted to receive said microfistula tube, whereby the inner tube may be used to push the microfistula tube into position and the innermost rod provides mechanical support during implantation of the microfistula tube;
2) mounting said microfistula tube on the innermost rod;
3) pushing the microfistula tube out of the outer tube and into a desired location by means of the inner tube, the rod moving in unison with the inner tube and the microfistula tube; and
4) withdrawing the surgical instrument from the body;
wherein said desired location is the anterior chamber.

68. The method as claimed in claim 67 wherein the rod and inner tube are withdrawn into the outer tube before the inner tube, outer tube and rod are withdrawn from the body.

69. A method for the implantation of a microfistula tube comprising:
1) forming passage with an outer tube of a implantation system comprising:
   a microfistula tube comprising a biocompatible, soluble tube defining a drainage canal having an inner surface, and biological cells for forming a basement membrane or for forming an intracellular matrix and a basement membrane, wherein said soluble tube is coated with said biological cells, incorporates said biological cells or both incorporates and is coated with said biological cells; and
   a surgical instrument including said outer tube for penetrating body tissue, an inner tube, and an innermost rod; wherein said outer tube, said inner tube and said innermost rod are coaxial, said outer tube is adapted to receive said microfistula tube, whereby the inner tube may be used to push the microfistula tube into position and the innermost rod provides mechanical support during implantation of the microfistula tube, and wherein the surgical instrument is adapted to be manipulated by electric motors;
2) locating said microfistula tube in said outer tube forward of said inner rod;
3) advancing said microfistula tube to said implantation site with said inner rod;
4) withdrawing said outer tube partially, then withdrawing said inner rod partially, followed by withdrawing said inner rod and outer tube in unison, wherein said partial withdrawal of the outer tine continues until a forward end of said outer tube is in the anterior chamber of the eye—has been added;
5) withdrawing said innermost rod; and
6) withdrawing the surgical instrument.

70. A method for the implantation of a microfistula tube comprising:
1) forming a passage with an outer tube of a microfistula tube implantation system comprising:
   a microfistula tube comprising a biocompatible, soluble tube defining a drainage canal having an inner surface, and biological cells for forming a basement membrane or for forming an intracellular matrix and a basement membrane, wherein said soluble tube is coated with said biological cells, incorporates said biological cells or both incorporates and is coated with said biological cells; and a surgical instrument including an outer tube for cutting and penetrating body tissue, and an inner rod; wherein said outer tube and said inner rod are coaxial, said outer tube is adapted to receive said microfistula tube and said inner rod, and said outer tube has a sharp forward end for cutting body tissue, whereby the outer tube may be used to create a passage to an implantation site for said microfistula tube, said inner rod may be used to position a microfistula tube at said site, and said inner rod and outer tube may be withdrawn from said site leaving said microfistula tube in position at said site;

2) locating said microfistula tube in said outer tube forward of said inner rod;

3) advancing said microfistula tube to said implantation site with said inner rod;

4) withdrawing said outer tube partially, then withdrawing said inner rod partially, followed by withdrawing said inner rod and outer tube in unison, wherein said partial withdrawal of the outer tine continues until a forward end of said outer tube is in the anterior chamber of the eye—has been added;

5) withdrawing said inner rod; and 6) withdrawing the surgical instrument.

71. A microfistula tube comprising:

a biocompatible, soluble tube defining a drainage canal having an inner surface and, when said soluble tube is disposed in the body of a patient, said soluble tube is functional as a drainage tube and will eventually fully dissolve and be absorbed by the body;

biological cells for forming a basement membrane of for forming an intracellular matrix and a basement membrane;

wherein said soluble tube is coated with said biological cells, incorporates said biological cells or both incorporates and is coated with said biological cells, and wherein said microfistula tube is made of absorbable material; and wherein the microfistula tube has a rearward end having an increased outer perimeter size to prevent the microfistula tube from advancing beyond the point of implantation.

72. A microfistula tube comprising:

a biocompatible, soluble tube defining a drainage canal having an inner surface; and biological cells for forming a basement membrane or for forming an intracellular matrix and a basement membrane;

wherein said soluble tube is coated with said biological cells, incorporates said biological cells or both incorporates and is coated with said biological cells, and wherein said soluble tube is made of gelatin or collagen; and wherein the microfistula tube has a rearward end having an increased outer perimeter size to prevent the microfistula tube from advancing beyond the point of implantation.

73. A microfistula tube implantation system comprising:

a microfistula tube comprising a biocompatible, soluble tube defining a drainage canal having an inner surface and, when said soluble tube is disposed in the body of a patient, said soluble tube is functional as a drainage tube and will eventually fully dissolve and be absorbed by the body, and biological cells for forming a basement membrane or for forming an intracellular matrix and a basement membrane, wherein said soluble tube is coated with said biological cells, incorporates said biological cells or both incorporates and is coated with said biological cells, wherein the microfistula tube has a rearward end having an increased outer perimeter size to prevent the microfistula tube from advancing beyond the point of implantation; and a surgical instrument including an outer tube for cutting and penetrating body tissue, and an inner rod, wherein said outer tube and said inner rod are coaxial, said outer tube is adapted to receive said microfistula tube and said inner rod, and said outer tube has a sharp forward end for cutting body tissue, whereby the outer tube may be used to create a passage to an implantation site for said microfistula tube at said site, and said inner rod may be used to position a microfistula tube at said site, and said inner rod and outer tube may be withdrawn from said site leaving said microfistula tube in position at said site.

74. A method for the implantation of a microfistula tube comprising:

1) forming a passage with an outer tube of an implantation system comprising:

a microfistula tube comprising a biocompatible, soluble tube defining a drainage canal having an inner surface, and biological cells for forming a basement membrane or for forming an intracellular matrix and a basement membrane, wherein said soluble tube is coated with said biological cells, incorporates said biological cells or both incorporates and is coated with said biological cells; and a surgical instrument including said outer tube for cutting and penetrating body tissue, and an inner tube, and an innermost rod; wherein said outer tube, said inner tube and said innermost rod are coaxial, said outer tube is adapted to receive said microfistula tube, whereby the inner tube may be used to push the microfistula tube into position and the innermost rod provides mechanical support during implantation of the microfistula tube, and wherein the surgical instrument is adapted to be manipulated by electric motors;

2) locating said microfistula tube in said outer tube forward of said inner rod;

3) rotating said outer tube while forming said passage to aid in the cutting of the tissue;

4) advancing said microfistula tube to said implantation site with said inner rod;

5) withdrawing said outer tube;

6) withdrawing said innermost rod; and 7) withdrawing the surgical instrument.

75. A method for the implantation of a microfistula tube comprising:

1) forming a passage with an outer tube of a microfistula tube implantation system comprising:

a microfistula tube comprising a biocompatible, soluble tube defining a drainage canal having an inner surface, and biological cells for forming a basement membrane or for forming an intracellular matrix and a basement membrane, wherein said soluble tube is coated with said biological cells, incorporates said biological cells or both incorporates and is coated with said biological cells; and a surgical instrument including said outer tube for cutting and penetrating body tissue, and an inner rod; wherein said outer tube and said inner rod are coaxial, said outer tube is adapted to receive said microfistula tube and said inner rod, and said outer tube has a sharp forward end for cutting body tissue, whereby the outer tube may be used to create a passage to an implantation site for said microfistula tube, said inner rod may be used to position a microfistula tube at said site, and said inner rod and outer tube may be withdrawn from said site leaving said microfistula tube in position at said site;

2) locating said microfistula tube in said outer tube forward of said inner rod;

3) rotating said outer tube while forming said passage to aid in the cutting of the tissue;

4) advancing said microfistula tube to said implantation site with said inner rod;

5) withdrawing said outer tube;

6) withdrawing said inner rod; and 7) withdrawing the surgical instrument.

* * * * *

UNITED STATES PATENT AND TRADEMARK OFFICE
CERTIFICATE OF CORRECTION

PATENT NO. : 6,544,249 B1
APPLICATION NO. : 09/319028
DATED : April 5, 2003
INVENTOR(S) : Yu et al.

It is certified that error appears in the above-identified patent and that said Letters Patent is hereby corrected as shown below:

Column 8, line 43, claim 1 should read:
    1. A microfistula tube comprising:
    a biocompatible, soluble tube defining a drainage canal having an inner surface and, when said soluble tube is disposed in the body of a patient, said soluble tube is functional as a drainage tube and will eventually fully dissolve and be absorbed by the body; and
    biological cells for forming a basement membrane or for forming an intracellular matrix and a basement membrane;
    wherein said soluble tube is coated with said biological cells, incorporates said biological cells or both incorporates and is coated with said biological cells, and wherein said microfistula tube is made of absorbable material wherein said microfistula tube has a rearward end having thicker walls to provide improved area and strength to allow the microfistula tube to be pushed into place by pressing against the rearward end of the microfistula tube.

Column 14, line 22, claim 69 should read:
    69. A method for the implantation of a microfistula tube comprising:
    1) forming a passage with an outer tube of a implantation system comprising:
    a microfistula tube comprising a biocompatible, soluble tube defining a drainage canal having an inner surface, and biological cells for forming a basement membrane or for forming an intracellular matrix and a basement membrane, wherein said soluble tube is coated with said biological cells, incorporates said biological cells or both incorporates and is coated with said biological cells; and
    a surgical instrument including said outer tube for penetrating body tissue, an inner tube, and an innermost rod; wherein said outer tube, said inner tube and said innermost rod are coaxial, said outer tube is adapted to receive said microfistula tube, whereby the inner tube may be used to push the microfistula tube into position and the innermost rod provides mechanical support during implantation of the microfistula tube, and wherein the surgical instrument is adapted to be manipulated by electric motors;
    2) locating said microfistula tube in said outer tube forward of said inner rod;
    3) advancing said microfistula tube to said implantation site with said inner rod;
    4) withdrawing said outer tube partially, then withdrawing said inner rod partially, followed by withdrawing said inner rod and outer tube in unison, wherein said partial withdrawal of the outer tine continues until a forward end of said outer tube is in the anterior chamber of the eye;
    5) withdrawing said innermost rod; and
    6) withdrawing the surgical instrument.

UNITED STATES PATENT AND TRADEMARK OFFICE
CERTIFICATE OF CORRECTION

PATENT NO.      : 6,544,249 B1
APPLICATION NO. : 09/319028
DATED           : April 5, 2003
INVENTOR(S)     : Yu et al.

It is certified that error appears in the above-identified patent and that said Letters Patent is hereby corrected as shown below:

Column 14, line 58 - column 15, line 26, claim 70 should read:

70. A method for the implantation of a microfistula tube comprising:
    1) forming a passage with an outer tube of a microfistula tube implantation system comprising:
    a microfistula tube comprising a biocompatible, soluble tube defining a drainage canal having an inner surface, and biological cells for forming a basement membrane or for forming an intracellular matrix and a basement membrane, wherein said soluble tube is coated with said biological cells, incorporates said biological cells or both incorporates and is coated with said biological cells; and
    a surgical instrument including an outer tube for cutting and penetrating body tissue, and an inner rod; wherein said outer tube and said inner rod are coaxial, said outer tube is adapted to receive said microfistula tube and said inner rod, and said outer tube has a sharp forward end for cutting body tissue, whereby the outer tube may be used to create a passage to an implantation site for said microfistula tube, said inner rod may be used to position a microfistula tube at said site, and said inner rod and outer tube may be withdrawn from said site leaving said microfistula tube in position at said site;
    2) locating said microfistula tube in said outer tube forward of said inner rod;
    3) advancing said microfistula tube to said implantation site with said inner rod;
    4) withdrawing said outer tube partially, then withdrawing said inner rod partially, followed by withdrawing said inner rod and outer tube in unison, wherein said partial withdrawal of the outer tine continues until a forward end of said outer tube is in the anterior chamber of the eye;
    5) withdrawing said inner rod; and
    6) withdrawing the surgical instrument.

Signed and Sealed this

Nineteenth Day of June, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,544,249 B1 |
| APPLICATION NO. | : 09/319028 |
| DATED | : April 8, 2003 |
| INVENTOR(S) | : Yu et al. |

It is certified that error appears in the above-identified patent and that said Letters Patent is hereby corrected as shown below:

Column 8, line 43, claim 1 should read:
    1. A microfistula tube comprising:
    a biocompatible, soluble tube defining a drainage canal having an inner surface and, when said soluble tube is disposed in the body of a patient, said soluble tube is functional as a drainage tube and will eventually fully dissolve and be absorbed by the body; and
    biological cells for forming a basement membrane or for forming an intracellular matrix and a basement membrane;
    wherein said soluble tube is coated with said biological cells, incorporates said biological cells or both incorporates and is coated with said biological cells, and wherein said microfistula tube is made of absorbable material wherein said microfistula tube has a rearward end having thicker walls to provide improved area and strength to allow the microfistula tube to be pushed into place by pressing against the rearward end of the microfistula tube.

Column 14, line 22, claim 69 should read:
    69. A method for the implantation of a microfistula tube comprising:
    1) forming a passage with an outer tube of a implantation system comprising:
    a microfistula tube comprising a biocompatible, soluble tube defining a drainage canal having an inner surface, and biological cells for forming a basement membrane or for forming an intracellular matrix and a basement membrane, wherein said soluble tube is coated with said biological cells, incorporates said biological cells or both incorporates and is coated with said biological cells; and
    a surgical instrument including said outer tube for penetrating body tissue, an inner tube, and an innermost rod; wherein said outer tube, said inner tube and said innermost rod are coaxial, said outer tube is adapted to receive said microfistula tube, whereby the inner tube may be used to push the microfistula tube into position and the innermost rod provides mechanical support during implantation of the microfistula tube, and wherein the surgical instrument is adapted to be manipulated by electric motors;
    2) locating said microfistula tube in said outer tube forward of said inner rod;
    3) advancing said microfistula tube to said implantation site with said inner rod;
    4) withdrawing said outer tube partially, then withdrawing said inner rod partially, followed by withdrawing said inner rod and outer tube in unison, wherein said partial withdrawal of the outer tine continues until a forward end of said outer tube is in the anterior chamber of the eye;
    5) withdrawing said innermost rod; and
    6) withdrawing the surgical instrument.

UNITED STATES PATENT AND TRADEMARK OFFICE
CERTIFICATE OF CORRECTION

PATENT NO. : 6,544,249 B1
APPLICATION NO. : 09/319028
DATED : April 8, 2003
INVENTOR(S) : Yu et al.

It is certified that error appears in the above-identified patent and that said Letters Patent is hereby corrected as shown below:

Column 14, line 58 - column 15, line 26, claim 70 should read:
   70. A method for the implantation of a microfistula tube comprising:
   1) forming a passage with an outer tube of a microfistula tube implantation system comprising:
   a microfistula tube comprising a biocompatible, soluble tube defining a drainage canal having an inner surface, and biological cells for forming a basement membrane or for forming an intracellular matrix and a basement membrane, wherein said soluble tube is coated with said biological cells, incorporates said biological cells or both incorporates and is coated with said biological cells; and
   a surgical instrument including an outer tube for cutting and penetrating body tissue, and an inner rod; wherein said outer tube and said inner rod are coaxial, said outer tube is adapted to receive said microfistula tube and said inner rod, and said outer tube has a sharp forward end for cutting body tissue, whereby the outer tube may be used to create a passage to an implantation site for said microfistula tube, said inner rod may be used to position a microfistula tube at said site, and said inner rod and outer tube may be withdrawn from said site leaving said microfistula tube in position at said site;
   2) locating said microfistula tube in said outer tube forward of said inner rod;
   3) advancing said microfistula tube to said implantation site with said inner rod;
   4) withdrawing said outer tube partially, then withdrawing said inner rod partially, followed by withdrawing said inner rod and outer tube in unison, wherein said partial withdrawal of the outer tine continues until a forward end of said outer tube is in the anterior chamber of the eye;
   5) withdrawing said inner rod; and
   6) withdrawing the surgical instrument.

This certificate supersedes Certificate of Correction issued June 19, 2007.

Signed and Sealed this

Seventh Day of August, 2007

JON W. DUDAS
*Director of the United States Patent and Trademark Office*